United States Patent [19]

Burke et al.

[11] Patent Number: 4,950,778

[45] Date of Patent: Aug. 21, 1990

[54] MANUFACTURE OF 5-CYANOVALERIC ACID AND ITS ESTERS USING CYCLIC COSOLVENTS

[75] Inventors: Patrick M. Burke; James B. Sieja, both of Wilmington, Del.

[73] Assignee: E. I. Du Pont de Nemours & Company, Wilmington, Del.

[21] Appl. No.: 434,866

[22] Filed: Nov. 8, 1989

Related U.S. Application Data

[63] Continuation-in-part of Ser. No. 283,159, Dec. 12, 1988, abandoned.

[51] Int. Cl.$^5$ ............................................. C07C 253/30
[52] U.S. Cl. ...................................... 558/353; 558/441
[58] Field of Search ........................................ 558/353

[56] References Cited

U.S. PATENT DOCUMENTS

| | | | |
|---|---|---|---|
| 2,820,059 | 1/1958 | Hasek et al. | 558/353 X |
| 3,028,419 | 4/1962 | Bloch | 558/353 X |
| 3,246,029 | 4/1966 | Kato et al. | 558/353 X |
| 4,060,543 | 11/1977 | Weitz et al. | 558/353 |
| 4,508,660 | 4/1985 | Sieja | 558/353 |

FOREIGN PATENT DOCUMENTS 1497046  1/1978  United Kingdom ................ 558/353

OTHER PUBLICATIONS

Falbe, New Syntheses with Carbon Monoxide, (1980), pp. 252–253, 302–303, Springer–Verlag, Berlin, Heidelberg, N.Y.

Fell, et al., [Translation of] Chem. Ztg., III, (1987), pp. 317–323.

Imyanitov, et al., [Translation of] Khimicheskaya Promyshlennost, 19, (1987), pp. 4–7.

Primary Examiner—Joseph Paul Brust

[57] ABSTRACT

Manufacture of 5-cyanovaleric acid by carbonylation of pentenenitriles from a mixture consisting essentially of pentenenitrile, CO and at least one compound of the formula ROH, where R is hydrogen or alkyl of 1 to 6 carbon atoms, and a cyclic urea and/or a cyclic amide, where the combined weight of the cosolvents is between about 70% and 99% of the total weight of the reaction mixture.

11 Claims, No Drawings

MANUFACTURE OF 5-CYANOVALERIC ACID AND ITS ESTERS USING CYCLIC COSOLVENTS

CROSS-REFERENCE TO RELATED APPLICATION

This application is a continuation-in-part of U.S. application Ser. No. 07/283,159 filed Dec. 12, 1988, now abandoned.

FIELD OF THE INVENTION

This invention relates to an improved process for the manufacture of 5-cyanovaleric acid and its esters in high selectivity from pentenenitriles.

BACKGROUND OF THE INVENTION

Processes for the preparation of 5-cyanovaleric acid from pentenenitriles by carbonylation in the presence of cobalt carbonyl catalysts are known. See, for example, U.S. Pat. No. 4,508,660 to Sieja where the reaction is carried out in a sulfone solvent, and U.S. Pat. No. 4,060,543 to Weitz, et al., where the reaction is carried out in the presence of basic heterocyclic compounds having a 5-membered or 6-membered nitrogen-containing ring, for example pyridine.

Wadden et al., British Patent 1,497,046, disclose a process for the manufacture of cyano-substituted aliphatic carboxylic esters which comprises reacting an alkenenitrile having at least 3 carbon atoms in the alkene residue with carbon monoxide and an alcohol under pressure in the presence of a catalyst. The reaction is preferably carried out in the presence of a weak organic base or of certain other compounds which function as Lewis bases, including pyridine, N-alkylpyrrolidones and caprolactam. Such compounds may comprise, for example, from 5 to 50% by weight of the reaction mixture.

It seems to be recognized in the art that the presence of pyridine, or certain substituted pyridines, in a carbonylation reaction mixture provides an increased yield in the straight chain isomers—See, for example: *Organic Chemistry and Technology, New Method of Production of Adipic Acid*, N. S. Imyanitov and E. N. Rakhlina, Khimicheskaya Promyshlennost, Vol. 19, No. 12, pp. 4–7. 1987; *Chem. Ztg.* 111 no 11:317-23 (1987) Hydrocarboxylation of Unsaturated Carboxylic Acids and Esters with Cobalt Carbonyl/Pyridine Complex Catalyst Systems by Bernhard Fell, Institute for Technical Chemistry and Petrochemistry of the RWTH Aachen, and Zilin Jin, Dalian Institute of Technology, Dalian/Peoples Republic of China; and *New Syntheses with Carbon Monoxide*, edited by J. Falbe, page 252, Springer-Verlag, Berlin, Heidelberg, New York, 1980.

SUMMARY OF THE INVENTION

It has now been found that 5-cyanovaleric acid and its esters can be obtained in high yield and high selectivity from any pentenenitrile, without the use of pyridine type promoters, and without the use of sulfone solvents. The process offers an advantage over the prior art processes, in that the yields of 5-cyanovaleric acid are higher when operating without a pyridine promoter. Moreover, subsequent removal of the pyridine promoters is obviated.

More particularly, a high yield process for the preparation of a compound having the formula:

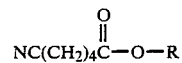

where R is hydrogen, or an alkyl radical having 1 to 6 carbon atoms, has been discovered. The process comprises reacting a mixture consisting essentially of pentenenitrile, carbon monoxide, at least one compound having the formula: ROH, where R is hydrogen or an alkyl radical having 1 to 6 carbon atoms, and one or more cosolvents selected from the class consisting of cyclic ureas having the formula

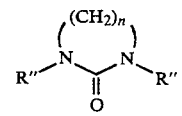

and cyclic amides having the formula:

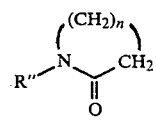

where n is 2 or 3 and R" is selected from hydrogen and alkyl groups having 1 to 6 carbon atoms, with a cobalt containing carbonylation catalyst, at a temperature in the range of about 130° to 220° C. and at a pressure of about 1500 to 8000 psi, where the combined weight of the cosolvents is between about 70% and about 99% of the total weight of the reaction mixture.

In most instances, the amount of cobalt containing carbonylation catalyst in the reaction should be about 0.5 to 5 parts by weight per 100 parts of pentenenitrile.

DETAILED DESCRIPTION

The cobalt containing carbonylation catalysts useful in the process of this invention are cobalt compounds including cobalt salts of Bronsted acids, carbon monoxide derivatives of cobalt and organometallic cobalt compounds. It is believed that cobalt carbonyl or cobalt carbonyl hydride is the active catalyst species and that it can be formed in situ from a variety of compounds such as those of the general types discussed above. Suitable salts are cobaltous and cobaltic chloride, iodide, bromide, propionate, butyrate, isobutyrate, acetate, carbonate, benzoate, valerate, 5-cyanovalerate, pentenoate, and hydroxide. Suitable organometallic cobalt compounds include dicyclopentadienyl cobalt, II-allyl cobalttricarbonyl, and II-crotyl cobalttricarbonyl. Compounds which are carbon monoxide derivatives of cobalt include dicobalt octacarbonyl, cobalt nitrosyltricarbonyl, cyclopentadienylcobalt dicarbonyl and tetracobalt-dodecacarbonyl.

The process of this invention can be used to convert any of the pentenenitrile isomers to 5-cyanovaleric acid or its esters, but 3-pentenenitrile (3PN) and 4-pentenenitrile (4PN) are somewhat more satisfactory than 2-pentenenitrile (2PN), in that the latter compound tends to yield more valeronitrile.

The R radical of the ROH compound can be hydrogen, methyl, ethyl, propyl, butyl, pentyl, or hexyl, preferably hydrogen or methyl. Mixtures of ROH compounds can also be used, for example, water and methanol. Because the reaction is slower when no water is present, it is preferable to use water, or a mixture of water with one or more other ROH compounds. When ROH is water, the product is 5-cyanovaleric acid; alcohols give the corresponding ester products and alcohol/water mixtures give mixed products. It is desirable that the amount of the ROH compound in the reaction mixture be at least stoichiometrically equivalent to the amount of pentenenitrile. The ROH compound can be present in large excess of the pentenenitrile.

One or more cosolvents selected from the class consisting of cyclic ureas having the formula:

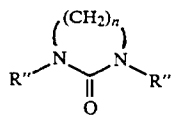

and cyclic amides having the formula

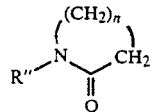

where n is 2 or 3 and R" is selected from hdyrogen and alkyl groups having 1 to 6 carbon atoms, are included in the reaction mixture. The cosolvents can be present in amounts from about 2 to 100 times on a weight basis the amount of ROH compound, provided that the combined weight of the cosolvents is between about 70% and about 99% of the total weight of the reaction mixture. Specific cyclic urea solvents that may be used are N,N'-dimethylethyleneurea (also called 1,3-dimethyl-2-imidazolidinone); and N,N'-dimethyl-propyleneurea. Specific cyclic amides that may be used are 2-pyrrolidinone; N-methyl-2-pyrrolidinone; 2-piperidone; and N-methyl-2-piperidone.

EXAMPLES

EXAMPLE 1

Hydrocarboxylation of trans-3-Pentenenitrile in N-Methylpyrrolidinone at 200° C.

A 300 mL Hastelloy-C mechanically stirred autoclave was flushed with nitrogen and then with high purity carbon monoxide. The autoclave was then charged with 150 ml of a solution of N-methylpyrrolidinone (NMP) containing 24.3 g of trans-3PN (300 mmoles) and 5.12 g dicobalt octacarbonyl (30 mequiv. of cobalt). The autoclave was pressured with carbon monoxide to 2000 psi. The temperature was then raised to 200° C. Reaction was initiated by injecting 6.2 g of water (345 mmoles) into the reaction mixture. The pressure was immediately adjusted to 4000 psi with carbon monoxide. Carbon monoxide was continuously fed to the autoclave from a 500 mL reservoir at an initial pressure of 4450 psi so as to maintain the total pressure constant at 4000 psi. The reaction was allowed to run for a total of 5 h, after which it was cooled to 20° C. The excess carbon monoxide was vented through a control valve and the product was discharged. The autoclave was washed first with 150 mL methanol at 100° C. under autogenous pressure and then with 150 mL methanol at room temperature.

The product and washes from the autoclave were combined, 5.0 g of tetradecane (internal gas chromatography standard) was added and the solution was diluted to 500 mL with methanol. A sample for this solution, esterified by heating in a sealed vial at 90° C. for 14 h with trimethylorthoformate and sulfuric acid esterification catalyst, was analyzed as the methyl esters by capillary gas chromatography. Product accounting (moles of all products recovered divided by moles 3PN charged) was 95.1%. Correcting to 100% accounting, the analysis showed 87.4% nitrile conversion and the following yields: 80.8% 5-cyanovaleric acid+adipic acid (5CVA+AA); 9.1% branched C6 acids and 9.6% valeronitrile. Independent analyses showed that the ratio of 5CVA to AA in the product mixture before esterification was greater than 10:1, the additional AA was apparently formed during the analytical work-up. Linearity was 89.9%, where $$\text{linearity} = \frac{\text{linear difunctional products}}{\text{all difunctional products}}$$

EXAMPLE 2

Hydrocarboxylation of trans-3-Pentenenitrile in N-Methylpyrrolidinone at 180° C.

The procedure described in Example 1 was repeated except that the temperature was reduced to 180° C. and the reaction was allowed to run for 5 h. Analysis shosed 59.9% nitrile conversion and the following yields: 87.9% (5CVA+AA); 6.0% branched C6 acids; and 4.9% valeronitrile. Linearity was 93.6%.

EXAMPLE 3

Hydrocarboxylation of trans-3-Penetenenitrile in N-Methylpyrrolidinone at 160° C.

The procedure described in Example 1 was repeated except that the temperature was reduced to 160° C., the total pressure at temperature was 3000 psi and the reaction was allowed to run for 5 h. Analysis showed 12.2% nitrile conversioin and the following yields: 86.1% (5CVA+AA); 7.1% branched C6 acids; and 2.6% valeronitrile. Linearity was 92.4%.

EXAMPLE 4

Hydrocarboxylation of cis-2-Pentenenitrile in N-Methylpyrrolidinone at 200° C.

The procedure described in Example 1 was repeated except that the trans-3PN was replaced with an equal weight of cis-2-pentenenitrile and the reaction was allowed to run for 3 h. Analysis showed 75.3% nitrile conversion and the following yields: 72.8% (5CVA+AA); 8.3% branched acids; and 18.2% valeronitrile.

EXAMPLE 5

Hydrocarboxylation of 4-Pentenenitrile in N-Methylpyrrolidinone at 200° C.

The procedure described in Example 1 was repeated except that the reactor was charged with 75 mL of NMP solution containing 12.12 g of 4-pentenenitrile and 2.6 g of dicobalt octacarbonyl. The temperature was 200° C., the total pressure was 4000 psi, and the reaction was allowed to run for 2.5 h. Analysis showed 77.3% nitrile conversion and the following yields: 85% (5CVA+AA); 7.3% branched C6 acids; and 7.5% valeronitrile.

EXAMPLE 6

Carbomethoxylation of trans-3-Pentenenitrile in N-Methylpyrrolidinone at 160° C.

The procedure described in Example 3 was repeated except that the water was replaced with 19.2 g of methanol (600 mmole). Analysis showed 12.9% nitrile conversion and the following yields: 86.2% methyl-5-cyanovalerate (M5CV); 6.4% branched esters; and 3.3% methyl valerate.

EXAMPLE 7

Hydrocarboxylation of trans-3-Pentenenitrile in N,N'-Dimethylpropyleneurea at 180° C.

A 75 mL stainless steel shaker tube was charged with trans-3PN (3.24 g, 40 mmole), water (0.8 g, 44 mmole), N,N-dimethylpropyleneurea (40 mL), and dicobalt octacarbonyl (1.4 g, 8 mmole). The tube was closed, cooled to −78° C., evacuated and then pressured with carbon monoxide to 1500 psi. The tube was heated with agitation to 180° C. over about 25 min, after which the pressure was adjusted to 4000 psi with carbon monoxide. The temperature was maintained at 180° C. for 5 h, and then cooled to 0° C. The excess carbon monoxide pressure was slowly vented, the product was discharged and the tube was rinsed twice with 50 mL portions of methanol. The product and washings were combined, o-dichlorobenzene (2.0 g, internal GC standard) was added, and the solution was made up to 200 mL with methanol). The products were esterified as described in Example 1, and then analyzed as the methyl esters on a 30 m×0.25 mm DB-5 capillary column. The analysis showed 46% pentenenitrile conversion, 93.7% product accounting, and the following normalized yields: 86.6% (5CVA+AA); 7.8% branched C6 acids; and 5.6% valeronitrile. Linearity was 91.8%.

EXAMPLE 8

Hydrocarboxylation of trans-3-Pentenenitrile in 1,3-Dimethyl-2-Imidazolidone at 180° C.

The procedure described in Example 7 was repeated except that N,N-dimethylpropyleneurea was replaced with 1,3-dimethyl-2-imidazolidone (DMI). GC analysis of the products showed 65% pentenenitrile conversion, 90.1% product accounting, and the following normalized yields: 84.7% (5CVA+AA); 7.7% branched C6 acids; and 7.5% valeronitrile. Linearity was 91.6%.

EXAMPLE 9

Hydrocarboxylation of trans-3-Pentenenitrile in 1-Methyl-2-Piperidone at 180° C.

The procedure described in Example 7 was repeated except that N,N'-dimethylpropyleneurea was replaced with 1-methyl-2-piperidone. GC analysis of the product showed 28.5% pentenenitrile conversion, 94.2% product accounting and the following normalized yields: 84% (5CVA+AA); 10.9% branched C6 acids; and 5.1% valeronitrile. Linearity was 88.5%.

EXAMPLES 10-14

Hydrocarboxylation of trans-3-Pentenenitrile in N-Methylpyrrolidone at 180° C. and Varying Ratios of NMP-to-t3PN These Examples show the beneficial effects of carrying out the hydrocarboxylation at high concentrations of the cyclic amide, N-methylpyrrolidinone (NMP).

In each of these Examples, trans-3-pentenenitrile, NMP and water in the amounts shown in the Table were weighed into a glass liner, the solution cooled in dry ice, and dicobalt octacarbonyl (1.4 g, 8 mmole) added. The vessel was closed, placed in a 300 mL shaker tube, pressured to 1500 psi with carbon monoxide, and heated to 180° C. The pressure was then adjusted to 4000 psi, and heated to 180° C. The pressure was then adjusted to 4000 psi, and maintained at 4000 psi for 5 h.

After cooling and venting the vessel, the products were isolated, esterified using trimethylorthoformate and analyzed as the corresponding methyl esters on a CP-Wax-57 capillary GC column. The "reduced" products were largely valeronitrile and valeric acid; the "linear" products were largely 5-cyanovaleric acid and adipic acid.

TABLE 1

| | | | | | Hydrocarboxylation of trans-3-Pentenenitrile | | | | |
|---|---|---|---|---|---|---|---|---|---|
| Ex. | 3PN (g) | Water (g) | NMP mL | NMP Wt. % | % Conv. | % (5CVA + AA) | % Branch | % Red | % Lin. |
| 10 | 1.62 | 0.4 | 40 | 95 | 100 | 84.3 | 5.9 | 8.31 | 93.5 |
| 11 | 3.2 | 0.8 | 40 | 91 | 100 | 82.6 | 7.8 | 8.8 | 91.4 |
| 12 | 4.8 | 1.2 | 35 | 85 | 100 | 80.2 | 8.1 | 11.7 | 90.8 |
| 13 | 8.1 | 2.0 | 32 | 77 | 98.6 | 78.4 | 11.1 | 10.5 | 87.6 |
| 14 | 13 | 3.2 | 27.8 | 64 | 97.5 | 63.6 | 13.5 | 23.0 | 82.5 |

"% Branch" = (moles of branched products) × 100 / (total moles of product)

"% Red." = (moles of reduced products) × 100 / (total moles of product)

"% Lin." = (moles of linear products) × 100 / (total moles of products)

EXAMPLE 15

Hydrocarboxylation of trans-3-Pentenenitrile in 1,3-Dimethyl-2-imidazolidone at 180° C.

The procedure described above for Examples 10-14 was repeated using 9.72 g of trans-3-PN, 2.4 g of water, and 35 mL of 1,3-dimethyl-2-imidazolidone (DMI) in place of NMP. GC analysis of the products showed 99.5% pentenenitrile conversion, 85.8% product accounting, and the following normalized yields: 67.1% (5CVA+AA); 12.8% branched C6 acids; and 20.13% valeronitrile. Linearity was 84%.

COMPARATIVE EXAMPLES A-G

The procedure described above for Examples 10-14 was repeated using the amounts of trans-3-PN, water and solvent(s) listed in Table 2. Prior to esterification and GC analysis, pyridine was removed from the product mixtures of Examples D-F using a strong acid ion exchange resin.

TABLE 2

Comparative Examples of Hydrocarboxylation of trans-3-Pentenenitrile

| Ex. | 3PN (g) | Water (g) | Solv. mL | NMP Wt. % | % Conv. | % (5CVA + AA) | % Branch | % Red | % Lin |
|---|---|---|---|---|---|---|---|---|---|
| A | 3.2 | 0.8 | 31 NMP 19 TOL[a] | 61 | 100 | 61.8 | 6.8 | 31.5 | 90.1 |
| B | 3.2 | 0.8 | 20 NMP 20 TOL | 49 | 100 | 44.8 | 7.5 | 47.8 | 85.7 |
| C | 3.2 | 0.8 | 20 DMI 20 TOL | 49[b] | 100 | 30.4 | 5.7 | 63.9 | 84.2 |
| D | 3.2 | 0.8 | 40 PYR | 93[c] | 100 | 33.0 | 5.9 | 60.1 | 85.3 |
| E | 9.72 | 2.4 | 35 PYR | 74[c] | 90 | 41.1 | 9.0 | 49.9 | 82.1 |
| F | 3.2 | 0.8 | 20 PYR 20 TOL | 48[c] | 83 | 24.8 | 9.5 | 65.7 | 72.2 |

[a]TOL = toluene
[b]Wt. % DMI
[c]Wt. % PYR (pyridine)

"% Branch" = (moles of branched products) × 100 / (total moles of product)

"% Red." = (moles of reduced products) × 100 / (total moles of product)

"% Lin." = (moles of linear products) × 100 / (total moles of products)

These Comparative Examples demonstrate the use of toluene and/or pyridine cosolvents results in undesirably high levels of reduced products. Comparative Examples D-E particularly demonstrate that pyridine, a preferred cosolvent of the prior art, is not functionally equivalent to the cyclic urea and cyclic amide cosolvents used in the process of this invention: In the process of this invention, the amount of reduction has been shown to be low even at moderate levels of NMP and decreases as NMP concentration increases from 64 to 95 wt% (Ex. 10-14). By contrast, the amount of reduction in Comparative Ex. D-E is high and increases as the pyridine level increases from 74 to 93 wt %.

We claim:

1. A high yield process for the preparation of a compound having the formula

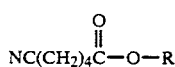

$$NC(CH_2)_4\overset{O}{\underset{\|}{C}}-O-R$$

where R is hydrogen or an alkyl radical having 1 to 6 carbon atoms, which comprises reacting a mixture consisting essentially of pentenenitrile, carbon monoxide, at least one compound having the formula: ROH, where R is hydrogen or an alkyl radical having 1 to 6 carbon atoms, and one or more cosolvents selected from the class consisting of cyclic ureas having the formula

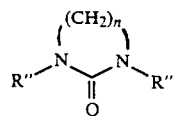

and cyclic amides having the formula

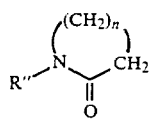

where n is 2 or 3 and R″ is selected from hydrogen and alkyl groups having 1 to 6 carbon atoms, with a cobalt containing carbonylation catalyst, at a temperature in the range of about 130° to 220° C. and at a pressure of about 1500 to 8000 psi, where the combined weight of the cosolvents is between about 70% and 99% of the total weight of the reaction mixture, where the amount of cobalt containing catalyst is in the range of 0.5 to 5.0 parts by weight per 100 parts of pentenenitrile, where the ROH compound is present in amount at least stoichiometrically equivalent to the pentenenitrile and the cosolvents are present in the amount of from about 2 to 100 times, on a weight basis, the weight of the ROH compound.

2. The process of claim 1 in which R is hydrogen and the cobalt catalyst is dicobalt octacarbonyl.

3. The process of claim 1 in which there are two compounds having the formula ROH in the reaction mixture.

4. The process of claim 3 in which one of the compounds is water and the other is methanol.

5. The process of claim 1 in which the cosolvent is N-methylpyrrolidinone.

6. The process of claim 1 in which the cosolvent is N,N′-dimethylpropyleneurea.

7. The process of claim 1 in which the pentenenitrile is 3-pentenenitrile.

8. The process of claim 1 in which the pentenenitrile is 2-pentenenitrile.

9. The process of claim 1 in which the pentenenitrile is 4-pentenenitrile.

10. The process of claim 1 in which the mixture consists of pentenenitrile, carbon monoxide, at least one compound having the formula ROH and one or more of the designated cosolvents.

11. A high yield process for the preparation of a compound having the formula

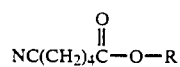

$$NC(CH_2)_4\overset{O}{\underset{\|}{C}}-O-R$$

where R is hydrogen or an alkyl radical having 1 to 6 carbon atoms, which comprises reacting a mixture consisting essentially of pentenenitrile, carbon monoxide, at least one compound having the formula: ROH, where R is hydrogen or an alkyl radical having 1 to 6 carbon atoms, and one or more cosolvents selected from the class consisting of cyclic ureas selected from the class consisting of N,N'-dimethylethyleneurea; N,N'-dimethylpropyleneurea, and cyclic amides selected from the class consisting of 2-pyrrolidinone; N-methyl-2-pyrrolidinone; 2-piperidone; and N-methyl-2-piperidone with a cobalt containing carbonylation catalyst, at a temperature in the range of about 130° to 220° C. and at a pressure of about 1500 to 8000 psi, where the combined weight of the cosolvents is between about 70% and 99% of the total weight of the reaction mixture, where the amount of cobalt containing catalyst is in the range of 0.5 to 5.0 parts by weight per 100 parts of pentenenitrile, where the ROH compound is present in amount at least stoichiometrically equivalent to the pentenenitrile and the cosolvents are present in the amount of from about 2 to 100 times, on a weight basis, the weight of the ROH compound.

* * * * *